(12) United States Patent
Bielenberg et al.

(10) Patent No.: US 12,252,654 B2
(45) Date of Patent: Mar. 18, 2025

(54) INTEGRATED BIOMASS GASIFICATION AND ELECTROLYSIS

(71) Applicant: ExxonMobil Technology and Engineering Company, Annandale, NJ (US)

(72) Inventors: James R. Bielenberg, Lebanon, NJ (US); Brandon J. O'Neill, Spring, TX (US); Zarath M. Summers, High Bridge, NJ (US)

(73) Assignee: ExxonMobil Technology and Engineering Company, Spring, TX (US)

( * ) Notice: Subject to any disclaimer, the term of this patent is extended or adjusted under 35 U.S.C. 154(b) by 341 days.

(21) Appl. No.: 17/451,694

(22) Filed: Oct. 21, 2021

(65) Prior Publication Data
US 2022/0119720 A1   Apr. 21, 2022

Related U.S. Application Data

(60) Provisional application No. 63/094,582, filed on Oct. 21, 2020.

(51) Int. Cl.
*C10J 3/72* (2006.01)
*B01J 6/00* (2006.01)
(Continued)

(52) U.S. Cl.
CPC ............... *C10J 3/72* (2013.01); *B01J 6/008* (2013.01); *C01B 3/24* (2013.01); *C10G 2/32* (2013.01); *C10J 3/721* (2013.01); *C10K 3/04* (2013.01); *C10L 1/04* (2013.01); *C12P 5/00* (2013.01); *C25B 1/04* (2013.01); *C25B 9/17* (2021.01); *H01M 8/06* (2013.01); *H01M 8/0668* (2013.01); *C01B 2203/0216* (2013.01); *C01B 2203/0283* (2013.01); *C01B 2203/061* (2013.01); *C01B 2203/062* (2013.01);
(Continued)

(58) Field of Classification Search
CPC ....... C10J 3/72; C10J 3/721; C10J 3/04; C10J 2300/0916; C10J 2300/1618; C10J 2300/1643; C10J 2300/0469; C01B 2203/0216; C01B 2203/0283; C01B 2203/061; C01B 2203/062; C01B 3/24; B01J 6/008; C10L 1/04; C10K 3/04
See application file for complete search history.

(56) References Cited

U.S. PATENT DOCUMENTS

| 7,976,797 B2 | 7/2011 | Chun et al. |
| 2005/0095183 A1* | 5/2005 | Rehmat .................. C10K 3/006 422/600 |

(Continued)

*Primary Examiner* — Matthew J Merkling
(74) *Attorney, Agent, or Firm* — Shook Hardy & Bacon LLP

(57) ABSTRACT

Systems and methods are provided for integration of electrolysis with biomass gasification to generate synthesis gas that can be used for production of renewable fuels and/or other hydrocarbonaceous compounds. The hydrocarbonaceous compounds can include compounds formed by chemical synthesis, such as alkanes formed by a Fischer-Tropsch process or methanol formed by a methanol synthesis process; or the hydrocarbonaceous compounds can include compounds formed by fermentation, such as alcohols formed by micro-organisms that use the synthesis gas as an input feed.

20 Claims, 1 Drawing Sheet

(51) Int. Cl.

| | |
|---|---|
| *C01B 3/24* | (2006.01) |
| *C10G 2/00* | (2006.01) |
| *C10K 3/04* | (2006.01) |
| *C10L 1/04* | (2006.01) |
| *C12P 5/00* | (2006.01) |
| *C25B 1/04* | (2021.01) |
| *C25B 9/17* | (2021.01) |
| *H01M 8/06* | (2016.01) |
| *H01M 8/0668* | (2016.01) |

(52) U.S. Cl.
CPC .................. *C10J 2300/0916* (2013.01); *C10J 2300/1618* (2013.01); *C10J 2300/1643* (2013.01); *C10L 2200/0469* (2013.01)

(56) References Cited

U.S. PATENT DOCUMENTS

| | | | |
|---|---|---|---|
| 2007/0220810 A1* | 9/2007 | Leveson | C10J 3/00 48/197 FM |
| 2009/0000184 A1* | 1/2009 | Garwood | B01F 27/412 44/307 |
| 2010/0273899 A1* | 10/2010 | Winter | C10L 5/44 518/703 |
| 2010/0317074 A1* | 12/2010 | Simpson | C12P 7/08 435/140 |
| 2011/0039956 A1* | 2/2011 | Raisz | C10J 3/02 518/712 |
| 2015/0337341 A1* | 11/2015 | Smart | C12P 7/18 435/158 |
| 2019/0153331 A1 | 5/2019 | Barrai et al. | |

* cited by examiner

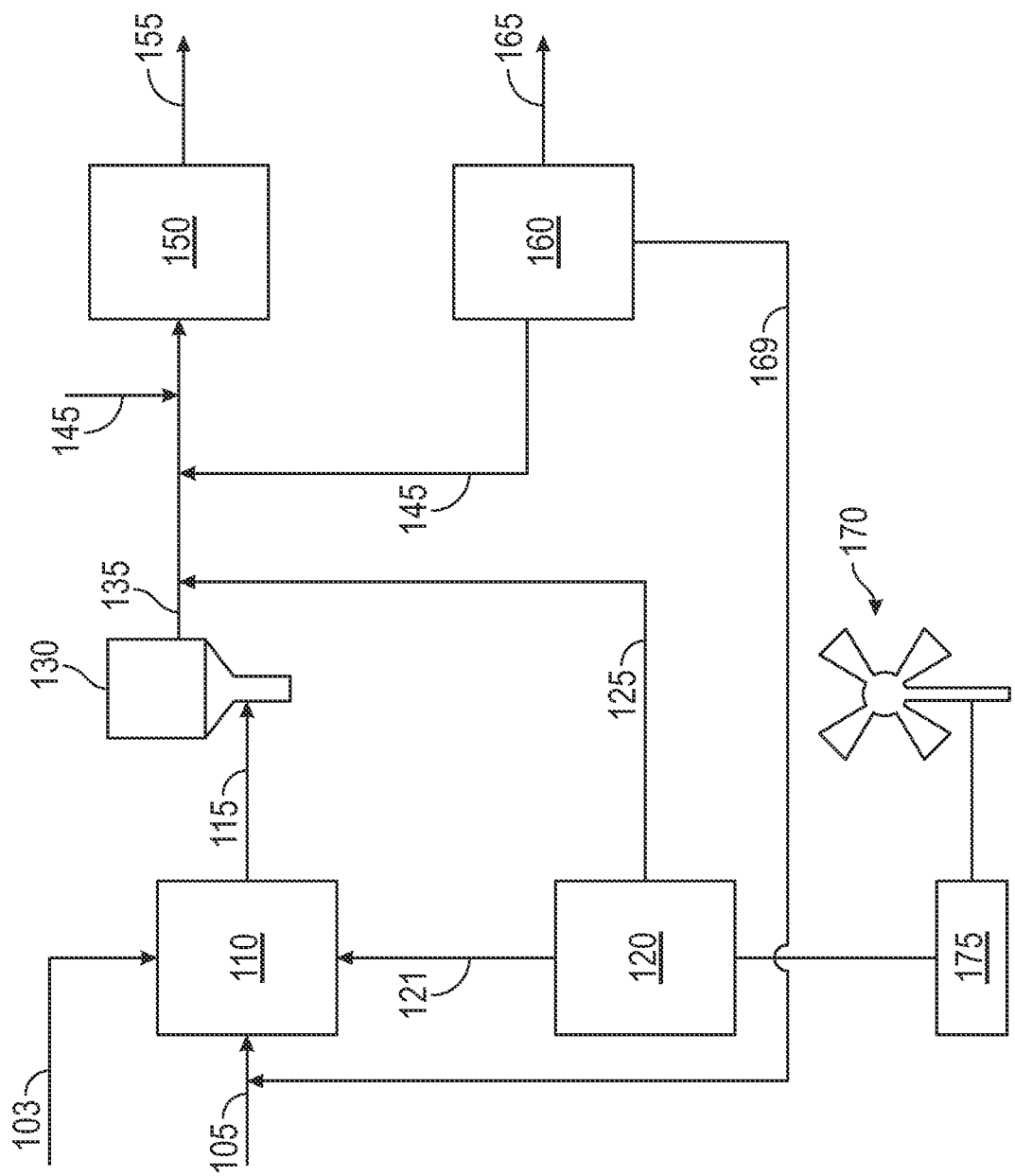

INTEGRATED BIOMASS GASIFICATION AND ELECTROLYSIS

CROSS-REFERENCE TO RELATED APPLICATIONS

This application claims the benefit of U.S. Provisional Application No. 63/094,582, filed Oct. 21, 2020, which is incorporated by reference herein in its entirety.

FIELD OF THE INVENTION

Systems and methods are provided for integration of biomass gasification systems with electrolysis systems for production of a synthesis gas. The resulting synthesis gas can then be used for production of renewable fuels and/or low carbon intensity fuels.

BACKGROUND OF THE INVENTION

One area of focus for reducing net greenhouse gas emissions from energy production is to use biomass as the source for at least part of the carbon in a fuel. Because biomass removes $CO_2$ from the environment as it grows, the net $CO_2$ generated by combustion of a fuel derived from biomass is offset by the $CO_2$ consumed during the growth of the biomass.

A number of barriers remain to efficient production of fuels from biomass. Some current strategies for conversion of biomass to fuels involve gasification of biomass to form synthesis gas. The synthesis gas can then be converted in one or more additional conversion processes into hydrocarbon-like compounds (such as alkanes or alcohols) for storage and/or transport. Unfortunately, the energy density of many types of biomass is substantially lower than the energy density of the desired hydrocarbon-like products. Due to this energy imbalance, substantial amounts of the carbon in the biomass can end up being converted into excess $CO_2$ that is not incorporated into a hydrocarbon-like product.

It would be desirable to have systems and methods for production of fuels from biomass that could reduce or minimize generation of excess $CO_2$ while forming hydrocarbon-like products that retain a substantial amount of renewable character. Preferably, the systems and methods can also reduce or minimize the amount of additional $CO_2$ production that is required in order to process the biomass and convert the resulting synthesis gas into hydrocarbon-like products.

U.S. Patent Application Publication 2005/0095183 describes a multi-stage gasification system for conversion of biomass or municipal solid waste into a synthesis gas product while reducing the amount of carbon char and/or tar in the product.

SUMMARY OF THE INVENTION

In various aspects, a method for forming renewable fuels is provided. The method includes exposing a feedstock comprising biomass to gasification conditions in a gasification reaction system to form at least a gasification output gas stream comprising $H_2$, CO, and $CO_2$. The gasification output gas stream can include a molar ratio of $H_2$ to CO of 1.5 or less. The gasification reaction system can include a reaction environment $O_2$ concentration. The method further includes performing electrolysis to form a first molar quantity of $H_2$ and a second molar quantity of $O_2$. The method further includes combining at least a portion of the gasification output gas stream with at least a portion of the first molar quantity of $H_2$ to form an enriched synthesis gas having a molar ratio of $H_2$ to CO of 1.8 to 2.2. The method further includes passing at least a portion of the second molar quantity of $O_2$ into the gasification reaction system to maintain the reaction environment $O_2$ concentration. Additionally, the method includes forming hydrocarbonaceous compounds from at least a portion of the enriched synthesis gas.

In various aspects, a gasification reaction system is provided. The gasification reaction system includes at least one gasification reactor comprising one or more gasifier inputs and a gasifier output. The system further includes an electrolyzer comprising an electrolyzer $O_2$ output in fluid communication with at least one gasifier input of the one or more gasifier inputs and an electrolyzer $H_2$ output. The system further includes a plurality of batteries for providing power to the electrolyzer. Additionally, the system includes a synthesis stage for formation of hydrocarbonaceous compounds, the synthesis stage being in fluid communication with the gasifier output and in fluid communication with the electrolyzer $H_2$ output. Optionally, the gasification reaction system further includes a renewable power source for providing power to the plurality of batteries, to the electrolyzer, or a combination thereof.

BRIEF DESCRIPTION OF THE DRAWINGS

The FIGURE shows an example of a configuration for integrating biomass gasification with electrolysis for production of hydrocarbonaceous fuels.

DETAILED DESCRIPTION OF THE INVENTION

All numerical values within the detailed description and the claims herein are modified by "about" or "approximately" the indicated value, and take into account experimental error and variations that would be expected by a person having ordinary skill in the art.

In various aspects, systems and methods are provided for integration of electrolysis with biomass gasification to generate synthesis gas that can be used for production of renewable fuels and/or other hydrocarbonaceous compounds. Optionally, at least a portion of the synthesis gas can be used directly as a renewable fuel. The hydrocarbonaceous compounds can include compounds formed by chemical synthesis, such as alkanes formed by a Fischer-Tropsch process or methanol formed by a methanol synthesis process; or the hydrocarbonaceous compounds can include compounds formed by fermentation, such as alcohols formed by micro-organisms that use the synthesis gas as an input feed. In this discussion, hydrocarbonaceous compounds are defined as compounds including at least one carbon atom, at least two hydrogen atoms, and where more than half of the atoms in the compound are either carbon or hydrogen. Examples of hydrocarbonaceous compounds include hydrocarbons (e.g., alkanes, alkenes, alkynes) and alcohols.

It has been discovered that synergistic benefits can be achieved by integrating electrolysis with biomass gasification to form a hydrogen-enriched synthesis gas for use in a synthesis and/or fermentation process for formation of hydrocarbonaceous fuels. To integrate electrolysis with biomass gasification, the hydrogen generated by electrolysis can be used to supplement the hydrogen content of the synthesis gas generated by biomass gasification. The resulting synthesis gas can be referred to as an enriched synthesis gas. It has been unexpectedly discovered that for some types of biomass, the electrolysis reaction to generate the supplemental hydrogen also results in generation of a desirable amount of oxygen for providing the oxygen in the biomass gasification environment. This means that both the hydrogen and the oxygen products from electrolysis can be used, as opposed to conventional electrolysis plants where the oxygen is simply a side product that is easily disposed of Additionally, because the oxygen from electrolysis has a relatively high purity, using the oxygen from hydrolysis as the oxygen source for gasification can reduce or minimize the amount of diluent gases that are introduced into the biomass gasification environment. Still further benefits can be achieved when the electrolysis reaction is operated at least in part by using a renewable power source such as solar power or wind power to provide electricity.

For many types of biomass, the yield of hydrocarbon (or hydrocarbonaceous) fuel from the biomass is initially limited based on differences in energy density. For example, a typical energy density for biomass is roughly 18 MJ/kg, while hydrocarbon fuels typically have an energy density of roughly 45 MJ/kg. Due to this energy difference, conventional processes for conversion of biomass to hydrocarbonaceous fuels typically incorporate less than 60% of the carbon from the biomass into the fuel. The remaining carbon leaves the conversion process as $CO_2$. This difference in energy density can also be characterized based on the composition of biomass and the resulting synthesis gas that is formed by gasification. Biomass typically has a hydrogen to carbon molar ratio of less than or equal to 2.0, and additionally biomass often includes a substantial oxygen content. As a result, gasification of biomass typically results in a synthesis gas (prior to water gas shift) with an $H_2$ to CO molar ratio of roughly 0.8 to 1.5, or 1.0 to 1.5, or 0.8 to 1.4, or 1.0 to 1.4. By contrast, a synthesis gas with an $H_2$ to CO molar ratio of 1.8 or more, or 2.0 or more is desirable for forming hydrocarbonaceous fuels. In some aspects, an enriched synthesis gas can have a $H_2$ to CO molar ratio of 1.8 or more, or 2.0 or more, such as 1.8 to 2.2, or 2.0 to 2.2.

The difficulties with using a synthesis gas with a low molar ratio of $H_2$ to CO are further compounded when the gasification is performed using air (or another dilute oxygen source) as the source of $O_2$ for the gasification environment. The substantial amount of $N_2$ present in air further reduces the energy content of the synthesis gas that is produced. Although an air separation unit can be used to generate a higher purity stream of oxygen, this also requires substantial additional energy to perform the separation. Unless a source of renewable energy is somehow available, the energy for operating the air separation unit is typically derived from combustion of fuels, leading to additional $CO_2$ production.

Forming hydrogen and oxygen by electrolysis of water is a well-known process. Although it would be desirable to use electricity provided from renewable sources (such as wind or solar) to form fuels, commercial application of electrolysis for production of renewable fuels has been limited so far. This is due in part to difficulties associated with long term storage of the direct products generated from a hydrolysis process. The direct products from electrolysis are molecular hydrogen and molecular oxygen. The molecular oxygen can typically be safely vented to the atmosphere if desired, so storage or disposal is only a minimal issue. However, long term storage and/or transport of hydrogen poses larger problems. While hydrogen can be safely stored, significant equipment is needed to maintain a desired level of safety. The options for transport of hydrogen are limited, as hydrogen cannot be transported via pipeline. Additionally, due to the difficulties in compressing hydrogen, the energy density of stored hydrogen can often be low.

An alternative to storing hydrogen directly can be to instead use the hydrogen generated by electrolysis to form hydrocarbonaceous fuels, such as alkanes or alcohols. By incorporating the hydrogen from electrolysis into hydrocarbonaceous fuels, the difficulties associated with fuel storage and transport can be reduced or minimized. However, conversion of the hydrogen into hydrocarbonaceous fuels requires performing some type of conversion process as well as providing a suitable source of carbon as a second input to the conversion process. An example of an option for providing carbon can be to extract $CO_2$ from air. While this can provide a high purity $CO_2$ stream, the cost of carbon extracted from air is typically greater than several hundred dollars per ton.

In various aspects, difficulties associated with formation of renewable fuels based on biomass and based on electrolysis can be reduced and/or minimized by integrating a biomass gasification process with a water electrolysis process. The integration of biomass gasification with water electrolysis for renewable fuels production can provide several types of synergistic benefits.

Some types of synergistic benefits can be related to using biomass gasification as a source of carbon for the hydrogen generated by electrolysis and/or using the hydrogen generated by electrolysis as a source of supplemental hydrogen for the synthesis gas generated by biomass gasification. The cost of carbon generated from biomass gasification is tied to the cost of the biomass feed and can often be less than one hundred dollars per ton. Thus, biomass gasification can provide a low cost source of carbon for use in combination with hydrogen generated from electrolysis. When viewed from the perspective of starting with biomass, combining hydrogen generated by electrolysis with electricity from a renewable source with synthesis gas generated by biomass gasification can provide a method for increasing the hydrogen content of the synthesis gas while reducing or minimizing any additional $CO_2$ that is generated during production of the supplemental hydrogen.

Other types of synergistic benefits can be based on the low hydrogen content of typical biomass feeds. Biomass feeds typically have a composition, prior to gasification, that includes roughly 50 wt % carbon, roughly 7 wt % hydrogen, and roughly 43 wt % oxygen. On a molar basis, this corresponds very roughly to having a molar ratio of carbon:hydrogen:oxygen of 4:7:2.8. It is noted that even with some variation, the ratio of carbon to hydrogen would be roughly 1:2 or less. As a result, when gasifying biomass to form synthesis gas, the $H_2$ to CO ratio of the resulting synthesis gas can tend to be near 1:1. A water gas shift reaction stage can be included to increase the $H_2$:CO ratio, but this also results in rejection of a substantial amount of $CO_2$. By contrast, when integrating biomass gasification with electrolysis, the electrolysis can be used to generate sufficient supplemental hydrogen so that the resulting enriched synthesis gas has an $H_2$:CO ratio of 1.8 to 2.2 without the need for additional shift reactions. This means that the water gas shift stage can be removed while still producing a high quality synthesis gas. In some aspects, the flow path for fluid communication between the output of the gasification reactor and the input for the fuel synthesis stage can be a flow path that is substantially free of catalyst that has water gas shift activity.

As a further synergistic benefit, it has been discovered that for selected biomass feeds, the amount of electrolysis that needs to be performed to generate supplemental hydrogen also corresponds to roughly the amount of electrolysis that needs to be performed to generate oxygen for the biomass gasification process. In other words, for biomass feeds having a target compositional profile, an electrolysis process can be used to provide both the oxygen for gasification and the supplemental hydrogen for improving the resulting synthesis gas. This allows the oxygen generated during electrolysis to be used as a process input, as opposed to simply venting the oxygen to the atmosphere. Additionally, the $O_2$ generated by electrolysis is typically of even higher purity than oxygen generated from an air separation unit. The availability of a high purity oxygen source means that the amount of $N_2$ and/or other diluent gases introduced into the gasification environment can be reduced or minimized. This can reduce equipment footprint and associated costs for performing the gasification process.

In various aspects, a biomass feed can be selected based on the hydrogen to carbon ratio in the feed, so that the amount of oxygen generated for biomass conversion can provide a corresponding amount of supplemental hydrogen that will result in a synthesis gas having roughly a 2:1 ratio of hydrogen to carbon. The selection of the biomass feed can be based on either a weight ratio or a molar ratio of hydrogen to carbon. The weight ratio of hydrogen to carbon in the biomass feed can be between 1:5 to 1:15, or 1:6 to 1:15, or 1:7 to 1:15, or 1:8 to 1:15. In terms of molar ratios, the molar ratio of hydrogen to carbon in the biomass feed can be between 2.4:1 to 0.7 to 1, or 2.1:1 to 0.7:1, or 1.9:1 to 0.7 to 1, or 1.7:1 to 0.7:1, or 1.5:1 to 0.7 to 1. Additionally, in some aspects, the carbon to oxygen molar ratio can also be considered. In such aspects, the carbon to oxygen weight ratio can be between 1.0:1 to 8.0:1, or 1.0:1 to 6.0:1. In terms of molar ratios, the carbon to oxygen molar ratio can be between 1.3:1 to 9.0:1, or 1.3:1 to 7.0 to 1, or 1.3:1 to 5.0:1.

Yet other benefits of integrating biomass gasification and electrolysis for hydrogen production can be realized by providing systems and methods that can allow the integrated process to continue to operate when swings in production of hydrogen occur due to intermittent availability of renewable power for electricity. For example, in some aspects, the power source for providing electricity for electrolysis can be wind power, solar power, or a combination thereof. The amount of available wind power and/or solar power can vary widely during a 12-hour period or 24-hour period. In some aspects, an integrated system for hydrocarbonaceous fuel production that includes both biomass gasification and electrolysis for hydrogen generation can be configured so that the system can continue to operate at a relatively stable level of biomass gasification even though the amount of power available from renewable sources is variable.

Attempting to operate a system for hydrocarbonaceous fuel production based on renewable energy sources with a relatively stable level of output poses problems due to the differences in time scale between biomass gasification and hydrogen generation by electrolysis. For electrolysis, the amount of hydrogen generated can vary directly with variations in the amount of available power. For power provided by wind energy or solar energy, variations in power generation can occur on the order of a few seconds or less, based on variations in wind gusts and cloud cover. By contrast, the conditions for biomass gasification require a longer time scale for adjustment. This is due in part to the need to create a high temperature reaction environment in order to perform gasification. Such a reaction environment can typically have a large thermal mass, so that it is difficult to change the temperature of the reaction environment on the time scale of seconds.

One option for improving the stability of operation for the biomass gasification process can be to have batteries associated with the electrolysis process. During operation, the amount of biomass gasification that is performed can be selected based on the storage level of the batteries. When the batteries are charged to a relatively high level, higher amounts of biomass gasification can be performed, with supplemental electricity being provided by the batteries if sufficient electricity is not directly available from the renewable source. When the batteries have a lower level of charge, a lower amount of biomass gasification can be performed. If additional renewable electricity becomes available, the additional electricity can be stored in the batteries. Because the batteries are being used to smooth out swings in the availability of the renewable electricity, a smaller amount of batteries are needed than would be required, for example, for long term storage of renewable electricity. Using batteries in this manner can allow renewable wind or solar power to be captured for long term use by converting the renewable power to a hydrocarbonaceous fuel while avoiding the need for an excessively large footprint of storage batteries.

Another option for improving the stability of operation for a biomass process can be related to configurations where fermentation is used to convert the enriched synthesis gas into hydrocarbonaceous fuels. In some aspects, the micro-organisms used for fermentation can correspond to micro-organisms that can perform the water gas shift reaction. By using such micro-organisms, the biomass gasification conditions can be selected to process a target flow rate of biomass by biomass gasification. When sufficient renewable energy is available for electrolysis, supplemental hydrogen can be provided to form an enriched synthesis gas. When there is not sufficient renewable energy to form an enriched synthesis gas, the ability of the micro-organisms to perform the water gas shift reaction can still allow the process to operate. The net amount of hydrocarbonaceous fuel that is produced may be reduced when the amount of renewable energy is decreased, but the biomass gasification process can operate with a reduced or minimized amount of swing in the biomass gasification feed rate and/or process conditions.

Electrolysis and Renewable Energy Sources

Electrolysis is a process that can be used to form molecular hydrogen and molecular oxygen from water. Equation 1 shows the stoichiometry.

$$2H_2O \Rightarrow 2H_2 + O_2 \qquad (1)$$

Based on the stoichiometry in Equation 1, in an idealized setting, the molar quantity of oxygen generated during electrolysis is half of the molar quantity of hydrogen generated during electrolysis. In other words, the ratio of the molar quantity of oxygen to the molar quantity of hydrogen is 0.50. In real systems, there could be some variation from the idealized stoichiometry, but generally the ratio of the molar quantity of oxygen to the molar quantity of hydrogen can be between 0.45 and 0.55.

Due to the nature of the electrolysis reaction and corresponding reaction environment, oxygen generated by an electrolyzer can have a relatively high purity. For example, an oxygen-containing stream generated by an electrolyzer can have an $O_2$ content of 99.5 vol % or more, or 99.6 vol % or more, such as up to 100 vol %. This is in contrast to an oxygen-containing stream generated by an air separation unit, which typically can have an $O_2$ content of 99.4 vol % or less.

An example of a reaction vessel for performing electrolysis is an electrolyzer. Many types of electrolyzers can be similar in construction to fuel cells, with the exception that current is received by the electrolyzer to cause electrolysis, as opposed to performing a fuel cell reaction where current is generated as an output by the fuel cell. In an electrolyzer, hydrogen is formed at the cathode while anode is formed at the anode. The exact operation of the electrolyzer can depend on the type of electrolyzer. Examples of conventional electrolyzer configurations include polymer electrolyte membrane (PEM) electrolyzers, alkaline electrolyzers, and solid oxide electrolyzers.

One benefit of using renewable energy for performing electrolysis is that electrolyzers can typically operate at varying levels of electric current. So long as the appropriate temperatures are maintained inside the electrolyzer reaction environment, an electrolyzer can operate over a range of electric current levels. For large scale production of electricity, further flexibility can be achieved by having a large number of electrolyzers, with some electrolyzers potentially being taken off-line during periods where the average amount of available renewable energy is reduced. The flexible nature of operation of electrolyzers can allow for increased production of hydrogen and oxygen during times when larger amounts of renewable energy are available (such as solar energy or wind energy).

The majority of the energy required by an electrolyzer corresponds to the energy required for performing electrolysis. Since electrolysis is performed using electrical energy, electrical energy generated by renewable sources can be used directly as the electric input for an electrolyzer. Alternatively, the electrical energy can be temporarily stored (e.g., in batteries) prior to being used in an electrolyzer to perform electrolysis.

It is noted that if sufficient renewable energy is available, other options could be available for production of $H_2$ without forming additional $CO_2$. For example, renewable energy could be used to power a steam methane reformer and a corresponding system for capturing the $CO_2$ created during the steam reforming process. Although this can provide the supplemental hydrogen for forming the synthesis gas, steam reforming does not produce a high purity oxygen stream.

Biomass Feedstock

Gasification of biomass is a desirable pathway for formation of carbon-based fuels and products, due in part to the potential for a sustainable cycle of carbon use. This is due in part to the nature of biomass, which can be grown and harvested on a relatively short time scale. When the biomass is converted to fuel products, the resulting $CO_2$ can be consumed to form new biomass.

The biomass used for gasification can be any convenient type of biomass. Some forms of biomass can include direct forms of biomass, such as algae biomass and plant biomass. Other forms of biomass may correspond to waste products, such as food waste, animal waste, paper, and/or other waste products originally formed from biomass materials. In this discussion, municipal solid waste is included within the definition of biomass, even though a portion of the solids in municipal solid waste may not strictly correspond to solids derived from biomass. In some aspects, the carbon to oxygen molar ratio of the biomass can be between 4:3 and 2:1, while the hydrogen to carbon molar ratio of the biomass can be between 2:1 and 1.5:1.

In aspects where the biomass is introduced into the gasification reactor at least partially as solids, having a small particle size can facilitate transport of the solids into the reactor. Smaller particle size can potentially also contribute to achieving a desired level of conversion of the biomass under the short residence time conditions. To prepare solids for gasification, the solids can be crushed, chopped, ground, or otherwise physically processed to reduce the median particle size to 3.0 cm or less, or 2.5 cm or less, or 2.0 cm or less, or 1.0 cm or less, such as down to 0.01 cm or possibly still smaller. For determining a median particle size, the particle size is defined as the diameter of the smallest bounding sphere that contains the particle.

Processing Conditions—Gasification

In various aspects, gasification of biomass can be used to generate a hydrogen-depleted synthesis gas that serves as one of the inputs for formation of hydrocarbonaceous fuels. Gasification is a process where sufficient oxygen is present in the reaction environment, with sufficiently severe conditions, to convert biomass (and/or other feed components to the gasification process) into solid char and synthesis gas components. Synthesis gas components include components that can be formed by the water gas shift reaction, so the synthesis gas components can include $H_2O$, $H_2$, CO, and/or $CO_2$. Under gasification conditions, less than 10.0 wt % of the gasification product can correspond to hydrocarbons, or less than 5.0 wt %, such as down to 0.1 wt % or possibly still lower. To the degree that hydrocarbons are formed, such hydrocarbons can primarily correspond to light gas components such as methane, ethane, or ethylene. Smaller amounts of heavier components, generally referred to as tars, are also present due to inefficiencies in the desired gasification reactions. To the degree atoms other than hydrogen, carbon, and oxygen are present in the gasification environment, other compounds can also be formed, such as sulfur-containing compounds or nitrogen-containing compounds.

In addition to biomass feedstock, another input flow for gasification can be an oxygen-containing gas flow. In the gasification environment, an equivalence ratio 0.25 to 0.40 can be beneficial for improving the yield of hydrogen during gasification. The equivalence ratio is defined as the ratio of the actual oxygen provided to the reactor relative to the amount of carbon, hydrogen, and oxygen in the gasification feedstock versus the stoichiometric ratio of oxygen to carbon, hydrogen, and oxygen that would be needed for complete combustion of the feedstock. Values of the equivalence ratio near zero indicate pyrolysis conditions. Values of the equivalence ratio near 1.0 or higher indicate conditions where combustion is likely to occur, rather than gasification.

One option for providing an oxygen-containing stream to the gasification reactor is to use the oxygen produced by electrolysis. In some aspects, using the oxygen produced by electrolysis can allow the oxygen-containing stream for gasification to have an oxygen content (i.e., a purity) of 99.5 vol % or more, or 99.6 vol % or more, such as up to 100 vol %. Optionally, the molar quantity of hydrogen that is used to form an enriched synthesis gas having a $H_2$ to CO ratio of 1.8 to 2.2 can correspond to substantially the same amount of electrolysis that provides a molar quantity of oxygen that is needed to achieve an equivalence ratio of 0.25 to 0.40. In such aspects, an electrolysis process can provide both the hydrogen for enriching the synthesis gas and the oxygen for the gasification reactor while reducing or minimizing the amount of excess $H_2$ or $O_2$. It is noted that this result can be achieved while avoiding exposure of the process output flow to a separate water gas shift reaction stage.

In other aspects, the oxygen from the electrolysis process may not be available for use, or the electrolysis process may not generate sufficient oxygen to provide an equivalence ratio of 0.25 to 0.40 for the reaction environment. For example, in aspects where the electrolysis process is powered at least in part using renewable energy, the amount of oxygen generated at a given point in time may be lower than the current input flow rate that is needed to maintain the gasification reaction. In such aspects, at least a portion of the oxygen-containing stream introduced into the gasification environment can correspond to oxygen from a lower purity oxygen-containing source, such as air. Such a lower purity oxygen-containing stream can have an oxygen content of 10 vol % to 70 vol %, or 10 vol % to 50 vol %, or 10 vol % to 30 vol %.

In some alternative aspects, it is noted that biomass gasification can also be carried out directly through the use of steam as both an oxygen source and a heat source often along with a secondary form of heating such as a hot solid stream or direct energy input through a process like plasma or microwaves. In still other alternative aspects, it is noted that indirect gasification can be performed. In such alternative aspects, gasification can be performed using at least two reactors/reaction zones. A first reactor/reaction zone can correspond to a reactor for combusting fuel in the presence of heat transfer particles, while a second reactor/reaction zone containing the biomass can receive the heat transfer particles, which provide the energy to perform the gasification process.

Optionally, for solid forms of biomass, the biomass can first be prepared by cutting the biomass into small particles. The prepared feedstock can then be fed into a suitable gasification reactor, such as a fluidized bed thermal cracker. The feedstock is then heated to a temperature between 500° C.-1500° C. and exposed to an equivalence ratio of 0.25 to 0.40 for a reaction time to perform gasification. The reaction time at a temperature of 500° C. or more can be 1.0 seconds to 10 seconds. In some aspects, a diluent stream of steam can also be fed into the reactor as a fluidizing gas. The weight ratio of steam to feedstock can be between 0.3:1 to 10:1.

The heating and cooling of the feedstock/gasification products can be performed in any convenient manner that allows for rapid heating of the feedstock. In some optional aspects, at least a portion of the heating of the feedstock to the gasification temperature can be performed at a heating rate of 100° C./sec or more, or 200° C./sec or more, such as up to 1000° C./sec or possibly still faster. As an example, in an aspect where the gasification reactor corresponds to a fluidized bed, the heating of the feedstock can be performed by mixing the feedstock with heated fluidizing particles. Sand is an example of a suitable type of particle for the fluidized bed. During operation, sand (or another type of heat transfer particle) can be passed into a regenerator to burn off coke and heat the particles. The heated particles can then be mixed with the feedstock prior to entering the reactor. By heating the heat transfer particles to a temperature above the desired gasification temperature, the heat transfer particles can provide at least a portion of the heat needed to achieve the gasification temperature. For example, the heat transfer particles can be heated to a temperature that is greater than the desired gasification temperature by 100° C. or more. Optionally, if the feedstock, sand, and fluidizing steam does not provide sufficient material to form a fluidized bed, additional fluidizing gas can be added, such as additional nitrogen, but this also will cause a corresponding increase in the volume of gas flow that needs to be handled during product recovery. After exiting from the gasification reactor, the heat transfer particles can be separated from the gasification effluent using a cyclone or another solid/vapor separator. Such a separator can also remove any other solids present after gasification. Optionally, in addition to a cyclone or other primary solid/vapor separator, one or more filters can be included at a location downstream from the cyclone to allow for removal of fine particles that become entrained in the vapor phase.

After removing solids, the products can be cooled using a heat exchanger (or another convenient method) to a temperature of 300° C. to 500° C. to stop the reaction and recover the heat. After solids removal, the composition of the synthesis gas portion ($H_2$, CO, $CO_2$, $H_2O$) of the resulting gas phase effluent can have a molar ratio of $H_2$ to CO of 0.8 to 1.5, or 1.0 to 1.5, or 0.8 to 1.4, or 1.0 to 1.4. The relative amounts of other components, such as the ratio of $H_2$ to $H_2O$, can vary depending on various factors, including whether steam was used as a fluidizing gas, the amount of oxygen in the feedstock, and whether other sources of water were present in the feedstock and/or processing environment.

Another example of a suitable reactor for performing gasification is a reverse flow reactor. Reverse flow reactors are described, for example, in U.S. Pat. No. 7,976,797 and U.S. Patent Application Publication 2019/0153331, which are incorporated herein by reference for the limited purpose of describing a suitable environment for performing a pyrolysis reaction, such as a biomass gasification reaction. A reverse flow regenerative reactor is a reactor or reactor system, whereby materials flow therein for a period of time in one direction through all or selected portions of the reactor and react or are otherwise processed therein. The direction of flow is then reversed and other materials are fed from the opposite direction through the reactor to displace any remaining first materials or reaction products back in the direction opposite from the original flow. The introduced other materials also flow through the reactor for gasification therein. Thereby, the reactor bed or reactor media components are exposed to materials flowing in each direction through the reactor. Heat may be produced or added by the reactants flowing in one direction and that heat may be used to pyrolyze/gasify or otherwise facilitate product-generating reactions in the reactor. A substantial part of the heat is then removed during flow in the other direction. The reactor system includes one or more hot or heated reaction zones and a lower temperature quenching zone that serves to absorb heat from the reacted product to quench the reaction process. After cooling the reaction product, the heated quench zone is cooled by reversing the direction of flow through the reactor and feeding new supply of materials through the quench zone to absorb the quench zone heat and carry that heat back to the reaction zone where the recovered heat is conserved and reused to pre-heat the reaction zone and reactant materials. After reaction of the pre-heated reactants, the reactor is "regenerated" and ready to gasify the hydrocarbonaceous reactant material (including any diluents or co-feeds) flowing through the reactor system in the opposite direction.

At least a portion of the feedstock that is transferred to or fed into the reactor system is, generally, (i) gasified in the reaction zone to form the gasification product, and (ii) that gasification reaction product from (i) is quenched in the quenching zone to stop the reaction. If the reaction is not timely quenched and stopped, the reaction may continue decomposing the molecules into coke, elemental components, or other less desirable reaction product components. Separated but simultaneous introduction of two or more reactants into the reactor system, such as through separate flow channels, can facilitate deferred reaction or combustion of the reactants until they are combined with each other, within the desired reactor zone to react with each other within that designated zone. Thereby, a heat bubble may be controllably and repeatedly positioned within the reactor system. In some embodiments, the reverse flow regenerative reactor may be described as comprising two zones/reactors: (1) a heat recuperating (first) zone/reactor, such as for quenching; and (2) a reforming (second) zone/reactor, such as for gasification or reforming. In some embodiments, however, the first and second reactors need not necessarily be separate components, but instead may be merely different sections of a common reactor. A reactant mixer may be provided intermediate the first and second reactors to assist with mixing and reacting of the separately introduced reactants.

The requisite high temperature required for gasification may be achieved by creating a high-temperature heat bubble in the middle of the reactor system or within one of the reactors of the reactor system, such as in packed or monolithic bed system. This heat bubble may be created via a two-step process wherein heat is (1) added to the reactor bed via delayed or deferred, in-situ combustion, and then (2) removed from the bed via in-situ endothermic reforming.

Conceptually, a regenerative reverse-flow thermal reactor can encompass a reaction region which is abutted by first and second heat transfer zones. The reaction region can encompass a gasification zone and a combustion zone. This description is conceptual in that, e.g., the gasification zone and combustion zone can occupy substantially the same (or overlapping) physical space within the reactor, albeit at different times. Methods used to establish initial conditions in these zones at the start of operation are not critical. For example, if the reactor is to begin in gasification mode, conventional methods can be used to preheat the reactor's first heat transfer zone and precool the second heat transfer zone, but the invention is not limited thereto. During gasification mode, heat is transferred from the reactor to feed in first heat transfer zone. Sufficient heat is transferred in the first heat transfer zone to gasify the heated feed in gasification zone. Effluent from the gasification zone (gasification product) is cooled by a transfer of heat to the reactor in second heat transfer zone, which rapidly quenches the gasification product. Condensable constituents that may be present in the gasification product typically deposit in the second heat transfer zone. The process gas, which typically comprises the remainder of the gasification product, is conducted away via line as shown. The gasification is carried out for a time under gasification conditions which establish a desired (typically predetermined) approach temperature at the start of at reactor location Y. Since the gasification is on average endothermic, gasification s mode is periodically switched to heating mode, which reheats the reactor for continued gasification and to establish a desired (typically predetermined) approach temperature at reactor location. A useful feature of regenerative reverse-flow thermal reactors is that at least part of the heat removed from the gasification product during the quenching (less any radiative, conductive, and convective losses) is stored in the reactor's second heat transfer zone and is available for transfer during regeneration mode operation. Another useful feature is that at least part of the heat removed from the combustion effluent during the quenching (again, less any radiative, conductive, and convective losses) is stored in the reactor's first heat transfer zone and is available for transfer during gasification mode operation.

During regeneration mode, which is carried out in an average flow direction that is substantially the reverse of the gasification flow direction, oxidant and fuel are introduced into the reactor via line, which typically comprises substantially separate fuel channels and oxidant channels. The fuel and oxidant are conveyed through the second heat transfer zone toward the combustion zone. Sufficient heat is transferred from the reactor in second heat transfer zone to the fuel and air for these to combust in combustion zone. Heat is transferred from the combustion effluent to reactor first heat transfer zone. Thus, the first and second heat transfer zones are regenerated for a following forward-flow thermal gasification interval, and the desired approach temperature is established at reactor location for carrying out gasification mode.

Synthesis of Hydrocarbonaceous Compounds—Catalytic Conversion of Synthesis Gas

In some aspects, the enriched synthesis gas formed from biomass gasification and electrolysis can be used for catalytic synthesis of hydrocarbonaceous compounds. Fischer-Tropsch synthesis of hydrocarbons and methanol synthesis are examples of catalyst synthesis pathways for converting synthesis gas to alkanes or alcohols.

One process for converting syngas to these products includes the Fischer-Tropsch process, in which syngas can be reacted over a catalyst at elevated temperature and pressure to produce long-chain hydrocarbons (or hydrocarbonaceous compounds) and oxygenates. The most common catalysts utilized can typically include iron-based catalysts (for so-called high-temperature-Fischer-Tropsch synthesis) and cobalt-based catalysts (for so-called low temperature-Fischer-Tropsch synthesis). Iron-based catalysts, along with other related catalysts, can also be referred to as shifting catalysts, as the water-gas shift reaction can tend to be readily equilibrated on these catalysts. Cobalt-containing catalysts and other related catalysts can be referred to as non-shifting, as they do not appear to substantially perform and/or catalyze the water-gas shift equilibration reaction at standard operating conditions. While other catalyst systems and process conditions may be employed, typical commercial operations can utilize a catalyst based on either cobalt or iron. In some preferred aspects, the largely saturated paraffins typically formed in Fischer-Tropsch product streams can be processed into high-value products such as diesel fuel, jet fuel, and lubricants, and/or can be utilized as blending stocks for those products.

Examples of suitable Fischer-Tropsch catalysts can generally include a supported or unsupported Group VIII, non-noble metal e.g., Fe, Ni, Ru, and/or Co, with or without a promoter e.g., ruthenium, rhenium, and/or zirconium. These Fischer-Tropsch processes can typically include fixed bed, fluid bed, and/or slurry hydrocarbon synthesis. In some aspects, a preferred Fischer-Tropsch process can be one that utilizes a non-shifting catalyst, such as based on cobalt and/or ruthenium, preferably comprising at least cobalt, and preferably a promoted cobalt, with the promoter comprising zirconium and/or rhenium, preferably being rhenium, although other promoter metals may also be used. The activities of these catalysts can be enhanced by the addition, optionally as part of a catalyst support, of a variety of metals, including copper, cerium, rhenium, manganese, platinum, iridium, rhodium, molybdenum, tungsten, ruthenium or zirconium. Such catalysts are well known, and a preferred catalyst is described in U.S. Pat. No. 4,568,663 as well as European Patent No. 0 266 898. The synthesis gas feed used in typical Fischer-Tropsch processes can comprise a mixture of $H_2$ and CO wherein $H_2$:CO are present in a ratio of 1.7 or more, or 2.1 or more, such as 1.7 to 2.5, or 2.1 to 2.5, or 1.7 to 2.1. Fischer-Tropsch processes can be implemented in a variety of systems such as fixed bed, slurry bed, and multiple channel designs. In various aspects, Fischer-Tropsch processes can be employed in a wide variety of reactors, such as small reactors (e.g. 1+ barrel/day) or in very large reactors (e.g. 10,000-50,000 barrels/day or more). The product, typically a hydrocarbon wax, can be used as is and/or can be converted to other (e.g. liquid) components by a variety of well-known chemical processes.

Generally, the Fischer-Tropsch process can be operated in the temperature range of 150° C. to 320 C (302° F.-626° F.) and at pressures ranging from 100 kPaa to 10 MPaa. Modifying the reaction conditions within the Fischer-Tropsch process can provide control over the yield and/or composition of the reaction products, including at least some control of the chain length of the reaction products. Typical reaction products can include alkanes (primary reaction product), as well as one or more of oxygenates, olefins, other hydrocarbonaceous compounds similar to hydrocarbons but which may contain one or more heteroatoms different from carbon and hydrogen, and various additional reaction by-products and/or unreacted feed components. These additional reaction products and feed components can include $H_2O$, unreacted syngas (CO and/or $H_2$), and $CO_2$, among other things. These additional reaction products and unreacted feed components can form a tail gas that can be separated from the primary reaction products of the Fischer-Tropsch process in gaseous form, as opposed to non-gaseous product, such as the more typical (desired) liquids and/or hydrocarbonaceous compounds generated by the process. When the goal of the Fischer-Tropsch process is synthesis of longer chain molecules, such as compounds suitable for use as a naphtha feed, a diesel feed, or other distillate boiling range molecules, some small ($C_1$-$C_4$) alkanes, olefins, oxygenates, and/or other hydrocarbonaceous compounds may be incorporated into the tail gas. The primary products from Fischer-Tropsch synthesis can be used directly, and/or can undergo further processing, as desired. For example, a Fischer-Tropsch synthesis process for forming distillate boiling range molecules can generate one or more product streams that can subsequently be dewaxed and/or hydrocracked in order to generate final products, e.g. with desired chain lengths, viscosities, and cold flow properties.

Methanol synthesis is another type of catalytic synthesis process. Methanol can typically be made from a syngas mixture, such as a mixture including CO, $H_2$, and optionally $CO_2$, at high pressure and temperature. Conventionally, the majority of methanol plants can utilize natural gas as a feedstock and can generate syngas by common processes like steam reforming, auto-thermal reforming, or partial oxidation. Most common configurations utilize a catalyst that can produce relatively low conversion per pass and can involve substantial recycle, along with production of various off-gasses and purge streams.

During methanol synthesis, carbon monoxide and hydrogen can react over a catalyst to produce methanol. Commercial methanol synthesis catalysts can be highly selective, with selectivities of greater than 99.8% possible under optimized reaction conditions. Typical reaction conditions can include pressures of 5 MPa to 10 MPa and temperatures of about 250° C. to about 300° C. With regard to the syngas input for methanol synthesis, the preferred ratio of $H_2$ to CO (2:1 $H_2$:CO) does not match the typical ratio generated by steam reforming. However, catalysts that facilitate methanol formation from syngas can sometimes additionally facilitate the water-gas shift reaction. As a result, the reaction scheme below in Equations 2 and 3 shows that $CO_2$ can also be used to form methanol:

$$2H_2 + CO \Rightarrow CH_3OH \tag{2}$$

$$3H_2 + CO_2 \Rightarrow CH_3OH + H_2O \tag{3}$$

For methanol synthesis reactions, the composition of the synthesis gas input can be characterized by the Module value M as shown in Equation 4.

$$M = [H_2 - CO_2]/[CO + CO_2] \tag{4}$$

Module values close to 2 can generally be suitable for production of methanol, such as values of M that are at least 1.7, or at least 1.8, or at least 1.9, and/or less than 2.3, or less than 2.2, or less than 2.1. As can be noted from the Module Value equation above, in addition to the ratio of $H_2$ to CO, the ratio of CO to $CO_2$ in the syngas can impact the reaction rate of the methanol synthesis reaction.

In a typical methanol plant, a large percentage of the reactor exhaust can be recycled after recovery of methanol liquid, due to low conversion per pass. As with most configurations featuring high recycle amounts, buildup of inerts to the process (e.g. methane) can require significant purge streams that can be rich in non-reactive components. At best, conventional configurations may burn the purge streams for heat integration, or more likely the purge streams can just be exhausted to the environment. It is noted that, in this type of conventional configuration, carbon not incorporated into the methanol can typically be exhausted to the environment, potentially resulting in high $CO_2$ emissions.

Synthesis of Hydrocarbonaceous Compounds—Fermentation

Another option for forming hydrocarbonaceous compounds can use micro-organisms to form products by anaerobic respiration or fermentation. Examples of fermentation products can include alcohols (such as ethanol or butanol) and acids (such as acetic acid). Processes for the production of ethanol and other alcohols from gaseous substrates are known.

A number of anaerobic bacteria are known to be capable of carrying out the fermentation of CO to alcohols, including n-butanol and ethanol, and acetic acid, and are suitable for use in the process of the present invention. Examples of such bacteria that are suitable for use in the invention include those of the genera *Acetitomaculum, Acetoanaerobium, Acetobacterium, Acetohalobium, Acetonema, Bryantella, Caloramator, Clostridium, Eubacterium, Holophaga, Moorella, Natroniella, Natronincola, Oxobacter, Ruminococcus, Sporomusa, Syntrophococcus, Tindallia, Thermoacetogenium, Thermoanaerobacter*, and *Treponema*. Culturing of the bacteria used in the methods of the invention may be conducted using any number of processes known in the art for culturing and producing substrates using anaerobic bacteria.

An example of a suitable environment for fermentation can be a bioreactor comprising one or more gas/liquid contact modules comprising multiple channels. Microorganisms can be inoculated into the bioreactor and a gaseous substrate provided, wherein microbial growth and metabolite production can occur. Additionally, or alternatively, the microorganism(s) can be cultured in a separate growth reactor and then substantially continuously provided to the bioreactor containing the module, wherein further growth, biofilm formation and/or metabolite production can occur.

The carbon source for the fermentation reaction can be a synthesis gas derived from biomass gasification, such as an enriched synthesis gas where the synthesis gas from biomass gasification is supplemented with hydrogen from electrolysis.

It will be appreciated that for growth of the bacteria and CO-to-alcohol fermentation to occur, in addition to the CO-containing substrate gas, a suitable liquid nutrient medium will need to be fed to the bioreactor. A nutrient medium will contain nitrogen, phosphorus, vitamins, and minerals sufficient to permit growth of the micro-organism used. Anaerobic media suitable for the fermentation of ethanol using CO as the sole carbon source are known in the art.

The fermentation should desirably be carried out under appropriate conditions for the desired fermentation to occur (e.g. CO-to-ethanol). Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition. The optimum reaction conditions will depend partly on the particular micro-organism used.

In some aspects, a microorganism with water gas shift activity can be used for the fermentation. In such aspects, hydrocarbonaceous compounds can be produced with widely varying quality for the synthesis gas delivered to fermentation. Although the yield of hydrocarbonaceous compounds may vary depending on the $H_2$ to CO molar ratio in the synthesis gas, the ability of the microorganisms to perform the water gas shift reaction can allow fermentation to continue even if the input synthesis gas has a relatively low molar ratio of $H_2$ to CO.

In such a case, a control system could be used to balance air/steam/$O_2$ flows to the gasifier to fix a constant biomass/oxygen ratio based on the availability of $O_2$ from electrolysis. In such a case, the quality of produced syngas (due to $O_2$/$N_2$ ratio in the feed and the availability of electrolytic $H_2$) would vary over short time periods. However, microorganisms are now available that can perform syngas fermentation while managing such swings in quality without operating upsets—i.e. ethanol yields as a function of syngas energy content remain fixed across varying syngas qualities. This type of system could provide a way to directly monetize renewable power to fuels without the need to invest in significant battery storage.

An additional benefit of performing fermentation is that the fermentation process also results in additional formation of biomass. In some aspects, the additional biomass formed during fermentation can be used to form at least part of the biomass feedstock for gasification.

Configuration Example

The FIGURE shows an example of a configuration for integration of biomass gasification with electrolysis. In the FIGURE, a biomass feedstock 105 is passed into a pyrolysis (gasification) reactor 110 that is operated under gasification conditions. An oxygen-containing stream 121 from electrolyzer 120 is also introduced into the gasification reactor. Additionally, optional steam input 103 can be introduced into the reactor, either separately or as part of another input stream. The gasification process results in a gasification output stream 115. The gasification output stream 115 can be separated 130 to separate particulates 132 (such as char particles or unreacted biomass) from a gasification synthesis gas stream 135. The synthesis gas stream 135 can then be combined with hydrogen-containing stream 125 from the electrolyzer 120 to form an enriched synthesis gas stream 145. The enriched synthesis gas stream 145 can then be passed into a stage for formation of hydrocarbonaceous compounds. In the FIGURE, both a catalytic synthesis stage 150 and a fermentation stage 160 are shown, but both catalytic synthesis stage 150 and fermentation stage 160 are optional. The catalytic synthesis stage can correspond to, for example, a Fischer-Tropsch reaction stage or a methanol synthesis stage. Catalytic synthesis stage 150 can generate at least a synthesized hydrocarbonaceous product stream 155. The fermentation stage 160 can correspond to, for example, a bioreactor including microorganisms for formation of alcohols or organic acids in a hydrocarbonaceous fermentation output 165. In aspects where fermentation stage 160 is used, at least a portion of biomass feedstock 105 can correspond to biomass 169 that is grown in fermentation stage 160.

Optionally, the electrical energy needed for operation of electrolyzer 120 can be provided from a renewable source 170. In such optional aspects, the renewable source 170 can provide electrical energy directly to electrolyzer 120 (not shown), or the electrical energy can be temporarily stored in batteries 175. Additionally or alternately, in aspects where electrolyzer 120 receives electrical energy directly or indirectly from renewable source 170, a microorganism can be used in fermentation stage 160 that has water gas shift capability.

Alternative Configuration—Anaerobic Digestion of Biomass

In some alternative aspects, instead of performing gasification on the biomass, the biomass can be converted to synthesis gas using anaerobic digestion. In such aspects, one option could be to use anaerobic digestion to create a methane/$CO_2$ (biogas) stream that can be directly reformed (dry reforming or steam methane reforming) into a syngas. Another option could be to develop a modified anaerobic digestion to convert biomass into a hydrogen/$CO_2$ synthesis gas directly through two routes of hydrogen production, dark fermentation or photofermentation of organic acids. There could also be improvements involving the introduction of non-reversible hydrogenases into either hydrogen production strains and the addition of compounds to block methanogenesis in these anaerobic digester systems. Examples of compounds to block methanogenesis can include, but are not limited to, nitrapyrin, 2-chloro-6-(trichloromethyl) pyridine, 2-bromoethanesulphonate, propynoic acid, nitroethane, ethyl trans-2-butenoate, 2-nitroethanol, sodium nitrate, and ethyl-2-butynoate.

Example 1—Biomass Gasification and Oxygen-Containing Streams

One of the advantages of integrating electrolysis with biomass gasification is that the electrolysis can provide both hydrogen for forming an enriched synthesis gas and high purity oxygen-containing stream for use in the gasification reaction environment. Using a high purity oxygen-containing stream can improve the initial quality of the synthesis gas formed from biomass gasification.

Table 1 shows a comparison of potential synthesis gas compositions that could be produced from biomass gasification. In Table 1, the first column corresponds to a predicted output gas composition (i.e., synthesis gas) based on published values for biomass gasification performed using air as the oxygen-containing stream, while the second column corresponds to a predicted output gas composition based on published values for biomass gasification performed using a high purity oxygen-containing stream having an oxygen content of 98 vol % or more (such as up to 100%).

TABLE 1

Predicted Synthesis Gas Compositions

| Gas Mole Fraction | Air as oxidant | $O_2$ as oxidant |
|---|---|---|
| $N_2$ | 46 vol % | 0 vol % |
| CO | 21 vol % | 40 vol % |
| $CO_2$ | 10 vol % | 20 vol % |
| $H_2$ | 16 vol % | 40 vol % |

It is noted that the values for the synthesis gas formed using air as the oxygen-containing stream do not add to 100%. The balance of the output gas composition when using air as the oxygen-containing stream corresponds to other components, including methane, water, and ammonia. As shown in Table 1, using a high purity oxygen-containing stream to achieve the desired equivalence ratio of 0.25 to 0.40 in the gasification environment can result in a gasification synthesis gas with an increased hydrogen content. In the example shown in Table 1, the $H_2$ to CO ratio when using air as the oxygen-containing stream is less than 0.8, while the $H_2$ to CO ratio for the high purity oxygen-containing stream is 1.0. Conventionally, a high purity oxygen-containing stream would require having an air separation unit associated with the gasification reactor. A separate source of hydrogen would also then be needed if it was desired to form an enriched synthesis gas stream. By contrast, using an electrolyzer can allow both hydrogen and oxygen to be provided to the gasification process and products.

Example 2—Comparison of Processes for Generating a Synthesis Gas

An average biomass composition can have a weight ratio of carbon:hydrogen:oxygen of roughly 50:7:43. For such an average biomass composition, conventional gasification can be performed using oxygen from an air separation unit. This would be expected to result in a synthesis gas having a composition of roughly 41 vol % $H_2$, 39 vol % CO, and 20 vol % $CO_2$. Thus, the expected synthesis gas from conventional gasification has a molar ratio of $H_2$ to CO of close to 1.0. A water gas shift reaction stage could be used to increase the $H_2$ to CO molar ratio to roughly 2.1. Substantial excess steam would be added to achieve this, and drive the reaction to the desired molar ratio. After water gas shift, a synthesis gas could be produced with a composition of roughly 38 vol % $H_2$, 18 vol % CO, 24 vol % $CO_2$, and 20 vol % $H_2O$. It is noted that the amount of $CO_2$ increased even though a substantial amount of steam was added to the composition. On a dry basis (no water), the composition would include roughly 47.5 vol % $H_2$, 22.5 vol % CO, and 30 vol % $CO_2$.

In contrast to the above situation, an integrated system could be used where electrolysis (preferably powered by renewable electricity) is used to provide both the $O_2$ for gasification and supplemental $H_2$ to enrich the synthesis gas. Because $O_2$ from an air separation unit was used in the first example, the expected synthesis gas from the gasification process would be expected be similar, or roughly 40 vol % $H_2$, 40 vol % CO, and 20 vol % $CO_2$. However, instead of using a water gas shift process to increase the ratio of $H_2$ to CO, the hydrogen generated by electrolysis can be added to the synthesis gas to form an enriched synthesis gas without formation of any excess $CO_2$. After addition of $H_2$ from electrolysis, the resulting enriched synthesis gas can have a composition of roughly 58.5 vol % $H_2$, 27.5 vol % CO, and 14 vol % $CO_2$. Thus, the amount of $CO_2$ in the enriched synthesis gas is roughly half or less of the $CO_2$ present in the synthesis gas formed by conventional gasification followed by water gas shift. This reduction in $CO_2$ can allow, for example, for substantial savings in carbon sequestration costs. This reduction in $CO_2$ also means that a substantially higher percentage of the carbon present in the biomass is incorporated into the hydrocarbonaceous compounds produced by the synthesis gas, rather than being rejected as $CO_2$.

Example 3—Additional Examples of Adding Supplemental Hydrogen from Electrolysis

To further illustrate the synergies of using electrolysis to provide oxygen as part of an integrated biomass gasification system, a comparison is provided for performing pyrolysis on three types of feeds. When performing biomass gasification, generating the oxygen for gasification also results in generation of a suitable amount of hydrogen to form an enriched synthesis gas with an $H_2$ to CO molar ratio of 1.8 to 2.2 (i.e., roughly 2.0) without having to be exposed to a water gas shift catalyst. By contrast, when feeds with a lower oxygen content and/or a lower carbon to hydrogen ratio are gasified, a synthesis gas having a molar ratio of $H_2$ to CO of roughly 2.0 can be generated without shifting prior to adding the supplemental hydrogen, or after adding only a small portion of the supplemental hydrogen. Additionally, when a feed with a high carbon to hydrogen ratio is gasified, addition of the supplemental hydrogen still results in an enriched synthesis gas product with an $H_2$ to CO ratio substantially below 2.0.

As one example, methane contains 25 wt % hydrogen and 75 wt % carbon. Gasification occurs at roughly 0.5 kg of $O_2$ per kg of methane. Gasification occurs according to the formula:

$$CH_4 + \tfrac{1}{2}O_2 \rightarrow CO + 2H_2 \,(H_2{:}CO \text{ ratio of } 2{:}1). \quad (1)$$

Of course, steam can be added to this process to use excess heat generated during gasification and to boost hydrogen content further. Since the basic gasification process tends to generate a synthesis gas with a $H_2$ to CO molar ratio of roughly 2.0, any addition of supplemental hydrogen from electrolysis will result in an enriched synthesis gas with an $H_2$ to CO molar ratio that is greater than 2.2. For most applications, increasing the $H_2$ to CO molar ratio of synthesis gas to values above 2.2 provides little additional benefit, so any advantage gained from adding the supplemental hydrogen is reduced or minimized.

The composition of biomass can change a great deal depending on biomass type and potential preprocessing of the feeds such as torrefaction. With that said, a composition of 50 wt % C, 7 wt % H, and 43 wt % O can be taken as representative.

To gasify this representative composition, oxygen derived from electrolysis can be used. In this example, the amount of oxygen used corresponds to an equivalence ratio of 0.4. Gasification at an equivalence ratio of 0.4 results in the composition shown in Table 2.

TABLE 2

Synthesis Gas from Gasification of Representative Biomass Composition

|  | wt % | Mole % |
|---|---|---|
| CO | 53% | 40% |
| $CO_2$ | 43% | 20% |
| $H_2$ | 4% | 40% |

As shown in Table 2, gasification of a representative biomass composition can result in a synthesis gas with an $H_2$ to CO molar ratio of roughly 1.0. However, the electrolysis used to generate the $O_2$ for the 0.4 equivalence ratio also resulted in generation of $H_2$. If the $H_2$ generated by the electrolysis reaction is added to synthesis gas shown in Table 2, the resulting enriched synthesis gas can have the molar composition (or volume composition) shown in Table 3.

TABLE 3

| Molar Composition of Enriched Synthesis Gas | |
|---|---|
| CO | 30% |
| $CO_2$ | 15% |
| Total $H_2$ | 55% |

The enriched synthesis gas composition shown in Table 3 has an $H_2$ to CO molar ratio of 1.83, which is in the range of 1.8 to 2.2. This represents a desirable synthesis gas composition that is formed by addition of a substantial portion (>80%) of the $H_2$ generated during electrolysis while also avoiding the need to have a water gas shift stage to arrive at an $H_2$ to CO molar ratio between 1.8 and 2.2.

For comparison, another potential gasification feed can be coal and/or petroleum coke. Both coal and petroleum coke can have carbon to hydrogen weight ratios of 15:1 or greater. The composition of coal can vary significantly but the U.S. Department of Energy has issued some general ranges on the composition of synthesis gas that is produced by coal gasification. The synthesis gas produced by coal gasification tends to have a much lower molar $H_2$:CO ratio. Coal gasification also requires significantly more oxygen to process via gasification as compared with gasification of biomass.

In order to provide a comparison, compositional data from an SRI report on the Shell coal gasification technology (SRI PEP Report 154A 2006) was used. In this report, Illinois #6 coal was used which is roughly 80% wt Carbon and only 5% H2 (both on a dry, ash free basis). The composition is shown in Table 4.

TABLE 4

| Representative Coal Composition Typical Composition of Coal - Illinois #6 | |
|---|---|
| C | 80.3 |
| H | 5.4 |
| O | 1.6 |
| S | 9.1 |
| N | 3.6 |

Gasification of coal can use a range of $O_2$ feedrates which will impact composition. In this example, an $O_2$ feedrate of 0.8 kg of $O_2$ per Kg of dry, ash free coal was used to generate the calculated synthesis gas composition shown in Table 5.

TABLE 5

| Synthesis Gas from Gasification of Coal | |
|---|---|
| Calculated Composition | vol % |
| $H_2$ | 30 |
| CO | 60 |
| $CO_2$ | 5 |
| $H_2O$ | 5 |

The synthesis gas shown in Table 5 is severely $H_2$ deficient ($H_2$:CO ratio of 0.5). Supplementing this synthesis gas with the $H_2$ produced during the electrolysis used to provide the $O_2$ for gasification would result in the enriched synthesis gas composition shown in Table 6.

TABLE 6

| Enriched Synthesis Gas from Coal Gasification (vol %) | |
|---|---|
| H2 | 53% |
| CO | 40% |
| CO2 | 4% |
| H2O | 3% |

Although an improvement, the enriched synthesis gas in Table 6 still has a $H_2$ to CO ratio of less than 1.3, which is well below the target range of 1.8 to 2.2.

Additional Embodiments

Embodiment 1. A method for forming renewable fuels, comprising: exposing a feedstock comprising biomass to gasification conditions in a gasification reaction system to form at least a gasification output gas stream comprising $H_2$, CO, and $CO_2$, the gasification output gas stream comprising a molar ratio of $H_2$ to CO of 1.5 or less, the gasification reaction system comprising a reaction environment $O_2$ concentration; performing electrolysis to form a first molar quantity of $H_2$ and a second molar quantity of $O_2$; combining at least a portion of the gasification output gas stream with at least a portion of the first molar quantity of $H_2$ to form an enriched synthesis gas having a molar ratio of $H_2$ to CO of 1.8 to 2.2; passing at least a portion of the second molar quantity of $O_2$ into the gasification reaction system to maintain the reaction environment $O_2$ concentration; and forming hydrocarbonaceous compounds from at least a portion of the enriched synthesis gas, the gasification conditions optionally comprising a temperature of 500° C. to 1500° C.

Embodiment 2. The method of Embodiment 1, wherein the at least a portion of the first molar quantity of $H_2$ comprises 80% or more of the first molar quantity of $H_2$, or wherein the at least a portion of the second molar quantity of $O_2$ comprises 80% or more of the second molar quantity of $O_2$, or a combination thereof.

Embodiment 3. The method of any of the above embodiments, wherein the biomass comprises a molar ratio of hydrogen to carbon of 2.1:1 to 0.7:1; or wherein the biomass comprises a and a molar ratio of hydrogen to carbon of 2.4:1 to 0.7:1 and a molar ratio of carbon to oxygen of 1.3:1 to 9.0:1; or a combination thereof.

Embodiment 4. The method of any of the above embodiments, wherein performing electrolysis comprises performing electrolysis using electricity derived from a renewable source.

Embodiment 5. The method of Embodiment 4, wherein a power of the electricity derived from a renewable source varies by 50% or more relative to a peak power of the electricity derived from the renewable source during a 12 hour period; or wherein at least a portion of the electricity derived from the renewable source is stored in one or more batteries prior to being used for performing electrolysis; or a combination thereof.

Embodiment 6. The method of any of the above embodiments, wherein forming hydrocarbonaceous compounds comprises fermentation of at least a portion of the enriched synthesis gas, the fermentation further comprising formation of additional biomass, wherein the feedstock comprising biomass optionally comprises at least a portion of the additional biomass.

Embodiment 7. The method of any of the above embodiments, wherein forming hydrocarbonaceous compounds comprises using at least a portion of the enriched synthesis gas as a feed for Fischer-Tropsch synthesis, methanol synthesis, or a combination thereof.

Embodiment 8. The method of any of the above embodiments, wherein the at least a portion of the second molar quantity of $O_2$ is passed into the gasification reaction system as an oxygen-containing gas flow comprising 99.6 wt % $O_2$ or more.

Embodiment 9. The method of any of Embodiments 1-8, the method further comprising: exposing the feedstock comprising biomass to second gasification conditions in the gasification reaction system to form at least a second gasification output gas stream comprising $H_2$, CO, and $CO_2$, the second gasification output gas stream comprising a second molar ratio of $H_2$ to CO that is lower than the molar ratio of $H_2$ to CO for the gasification output stream, the second gasification conditions comprising a reaction environment $O_2$ concentration that is at least partially maintained based on providing an oxygen-containing input stream with an oxygen content of 70 vol % or less; and forming hydrocarbonaceous compounds from at least a portion of the second gasification output stream.

Embodiment 10. The method of any of Embodiments 1-8, the method further comprising: exposing the feedstock comprising biomass to second gasification conditions in the gasification reaction system to form at least a second gasification output gas stream comprising $H_2$, CO, and $CO_2$, the second gasification output gas stream comprising a second molar ratio of $H_2$ to $C_2$ that is lower than the molar ratio of $H_2$ to CO for the gasification output stream, the second gasification conditions comprising a reaction environment $O_2$ concentration that is at least partially maintained based on providing an oxygen-containing input stream with an oxygen content of 70 vol % or less; performing electrolysis to form a third molar quantity of $H_2$ that is lower than the first molar quantity of $H_2$; combining at least a portion of the second gasification output gas stream with at least a portion of the third molar quantity of $H_2$ to form a second enriched synthesis gas having a molar ratio of $H_2$ to CO of less than 1.8; and forming hydrocarbonaceous compounds from at least a portion of the second enriched synthesis gas.

Embodiment 11. The method of Embodiment 9 or 10, the method further comprising: exposing a portion of the second gasification output stream or the second enriched synthesis gas to water gas shift conditions to form a shifted portion, wherein forming hydrocarbonaceous compounds from at least a portion of the second gasification output stream or at least a portion of the second enriched synthesis gas comprises forming hydrocarbonaceous compounds from the shifted portion.

Embodiment 12. The method of any of the above embodiments, wherein the at least a portion of the gasification output gas stream is combined with the at least a portion of the first molar quantity of $H_2$ without exposing the at least a portion of the gasification output gas stream to a catalyst having water gas shift activity; or wherein the gasification reaction system comprises an indirect gasification system, the indirect gasification system comprising at least a first reactor comprising the gasification conditions and at least a second reactor comprising the reaction environment $O_2$ concentration; or a combination thereof.

Embodiment 13. A gasification reaction system comprising: at least one gasification reactor comprising one or more gasifier inputs and a gasifier output; an electrolyzer comprising an electrolyzer $O_2$ output in fluid communication with at least one gasifier input of the one or more gasifier inputs and an electrolyzer $H_2$ output; a plurality of batteries for providing power to the electrolyzer; and a synthesis stage for formation of hydrocarbonaceous compounds, the synthesis stage being in fluid communication with the gasifier output and in fluid communication with the electrolyzer $H_2$ output, wherein the gasification reaction system optionally further comprises a renewable power source for providing power to the plurality of batteries, to the electrolyzer, or a combination thereof.

Embodiment 14. The gasification reaction system of Embodiment 13, wherein the synthesis stage comprises a fermentation stage and wherein the system further comprises a biomass growth stage in fluid communication with the fermentation stage and in solids flow communication with at least one gasifier input of the one or more gasifier inputs.

Embodiment 15. The gasification reaction system of Embodiment 13 or 14, wherein the synthesis stage is in fluid communication with the gasifier output via a first fluid communication flow path, the first fluid communication flow path being free of catalyst with water gas shift activity.

When numerical lower limits and numerical upper limits are listed herein, ranges from any lower limit to any upper limit are contemplated. While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

The present disclosure has been described above with reference to numerous embodiments and specific examples. Many variations will suggest themselves to those skilled in this art in light of the above detailed description. All such obvious variations are within the full intended scope of the appended claims.

What is claimed is:

1. A method for forming renewable fuels, comprising:
exposing a feedstock comprising biomass to gasification conditions in a gasification reaction system to form at least a gasification output gas stream comprising $H_2$, CO, and $CO_2$, the gasification output gas stream comprising a molar ratio of $H_2$ to CO of 1.5 or less, the gasification reaction system comprising a reaction environment $O_2$ concentration;
performing electrolysis to form a first molar quantity of $H_2$ and a second molar quantity of $O_2$;
combining at least a portion of the gasification output gas stream with at least a portion of the first molar quantity of $H_2$ to form an enriched synthesis gas having a molar ratio of $H_2$ to CO of 1.8 to 2.2;
passing at least a portion of the second molar quantity of $O_2$ into the gasification reaction system to maintain the reaction environment $O_2$ concentration;
forming hydrocarbonaceous compounds from at least a portion of the enriched synthesis gas;
exposing the feedstock comprising biomass to second gasification conditions in the gasification reaction system to form at least a second gasification output gas stream comprising $H_2$, CO, and $CO_2$, the second gasification output gas stream comprising a second molar ratio of $H_2$ to CO that is lower than the molar ratio of $H_2$ to CO for the gasification output stream, the second gasification conditions comprising a reaction environment $O_2$ concentration that is at least partially maintained based on providing an oxygen-containing input stream with an oxygen content of 70 vol % or less; and forming hydrocarbonaceous compounds from at least a portion of the second gasification output stream.

2. The method of claim 1, wherein the at least a portion of the first molar quantity of $H_2$ comprises 80% or more of the first molar quantity of $H_2$, or wherein the at least a portion of the second molar quantity of $H_2$ comprises 80% or more of the second molar quantity of $H_2$, or a combination thereof.

3. The method of claim 1, wherein the biomass comprises a molar ratio of hydrogen to carbon of 2.1:1 to 0.7:1.

4. The method of claim 1, wherein the biomass comprises a molar ratio of hydrogen to carbon of 2.4:1 to 0.7:1 and a molar ratio of carbon to oxygen of 1.3:1 to 9.0:1.

5. The method of claim 1, wherein performing electrolysis comprises performing electrolysis using electricity derived from a renewable source.

6. The method of claim 5, wherein a power of the electricity derived from a renewable source varies by 50% or more relative to a peak power of the electricity derived from the renewable source during a 12 hour period; or wherein at least a portion of the electricity derived from the renewable source is stored in one or more batteries prior to being used for performing electrolysis; or a combination thereof.

7. The method of claim 1, wherein forming hydrocarbonaceous compounds composes fermentation of at least a portion of the enriched synthesis gas.

8. The method of claim 7, wherein the fermentation further comprises formation of additional biomass, and wherein the feedstock comprising biomass comprises at least a portion of the additional biomass.

9. The method of claim 1, wherein forming hydrocarbonaceous compounds comprises using at least a portion of the enriched synthesis gas as a feed for Fischer-Tropsch synthesis, methanol synthesis, or a combination thereof.

10. The method of claim 1, wherein the at least a portion of the second molar quantity of $O_2$ is passed into the gasification reaction system as an oxygen-containing gas flow comprising 99.6 wt % $O_2$ or more; or wherein the gasification conditions comprise a temperature of 500° C. to 1500° C.; or a combination thereof.

11. The method of claim 1, the method further comprising:

exposing a portion of the second gasification output stream to water gas shift conditions to form a shifted portion of the second gasification output stream, wherein forming hydrocarbonaceous compounds from at least a portion of the second gasification output stream comprises forming hydrocarbonaceous compounds from the shifted portion of the second gasification output stream.

12. A method for forming renewable fuels, comprising:

exposing a feedstock comprising biomass to gasification conditions in a gasification reaction system to form at least a gasification output gas stream comprising $H_2$, CO, and $CO_2$, the gasification output gas stream comprising a molar ratio of $H_2$ to CO of 1.5 or less, the gasification reaction system comprising a reaction environment $O_2$ concentration:

performing electrolysis to form a first molar quantity of $H_2$ and a second molar quantity of $O_2$;

combining at least a portion of the gasification output gas stream with at least a portion of the first molar quantity of $H_2$ to form an enriched synthesis gas having a molar ratio of $H_2$ to CO of 1.8 to 2.2;

passing at least a portion of the second molar quantity of $O_2$ into the gasification reaction system to maintain the reaction environment $O_2$ concentration;

forming hydrocarbonaceous compounds from at least a portion of the enriched synthesis gas;

exposing the feedstock comprising biomass to second gasification conditions in the gasification reaction system to form at least a second gasification output gas stream comprising $H_2$, CO, and $CO_2$, the second gasification output gas stream comprising a second molar ratio of $H_2$ to CO that is lower than the molar ratio of $H_2$ to CO for the gasification output stream, the second gasification conditions comprising a reaction environment $O_2$ concentration that is at least partially maintained based on providing an oxygen-containing input stream with an oxygen content of 70 vol % or less;

performing electrolysis to form a third molar quantity of $H_2$ that is lower than the first molar quantity of $H_2$, combining at least a portion of the second gasification output gas stream with at least a portion of the third molar quantity of $H_2$ to form a second enriched synthesis gas having a molar ratio of $H_2$ to CO of less than 1.8; and forming hydrocarbonaceous compounds from at least a portion of the second enriched synthesis gas.

13. The method of claim 12, the method further comprising:

exposing a portion of the second enriched synthesis gas to water gas shift conditions to form a shifted portion of the second enriched synthesis gas, wherein forming hydrocarbonaceous compounds from at least a portion of the second enriched synthesis gas comprises forming hydrocarbonaceous compounds from the shifted portion of the second enriched synthesis gas.

14. The method of claim 1, wherein the at least a portion of the gasification output gas stream is combined with the at least a portion of the first molar quantity of $H_2$ without exposing the at least a portion of the gasification output gas stream to a catalyst having water gas shift activity.

15. The method of claim 1, wherein the gasification reaction system comprises an indirect gasification system, the indirect gasification system comprising at least a first reactor comprising the gasification conditions and at least a second reactor comprising the reaction environment $O_2$ concentration.

16. The method of claim 12, wherein the at least a portion of the first molar quantity of $H_2$ comprises 80% or more of the first molar quantity of $H_2$, or wherein the at least a portion of the second molar quantity of $H_2$ comprises 80% or more of the second molar quantity of $H_2$, or a combination thereof.

17. The method of claim 12, wherein the biomass comprises a molar ratio of hydrogen to carbon of 2.1:1 to 0.7:1.

18. The method of claim 12, wherein the biomass comprises a molar ratio of hydrogen to carbon of 2.4:1 to 0.7:1 and a molar ratio of carbon to oxygen of 1.3:1 to 9.0:1.

19. The method of claim 12, wherein performing electrolysis comprises performing electrolysis using electricity derived from a renewable source.

20. The method of claim 19, wherein a power of the electricity derived from a renewable source varies by 50% or more relative to a peak power of the electricity derived from the renewable source during a 12 hour period; or wherein at least a portion of the electricity derived from the renewable source is stored in one or more batteries prior to being used for performing electrolysis; or a combination thereof.

* * * * *